United States Patent [19]

Smith

[11] Patent Number: 5,156,633

[45] Date of Patent: Oct. 20, 1992

[54] MARYLAND DISSECTOR LAPAROSCOPIC INSTRUMENT

[75] Inventor: Kevin W. Smith, Miami, Fla.

[73] Assignee: Symbiosis Corporation, Miami, Fla.

[21] Appl. No.: 680,390

[22] Filed: Apr. 4, 1991

Related U.S. Application Data

[63] Continuation-in-part of Ser. No. 521,766, May 10, 1990.

[51] Int. Cl.$^5$ .............................................. A61B 17/00
[52] U.S. Cl. .................................. 606/205; 128/751; 606/174; 606/170; 30/251
[58] Field of Search ................... 30/251, 250, 242, 155, 30/266, 267, 335; 403/79; 128/749, 751; 606/205, 206, 207, 208, 167, 170, 174

[56] References Cited

U.S. PATENT DOCUMENTS

| | | | |
|---|---|---|---|
| 9,241 | 6/1880 | Willson | 403/113 |
| 154,710 | 9/1874 | Olin | 403/116 |
| 1,038,184 | 9/1912 | Norumilly | 403/113 |
| 1,645,981 | 10/1927 | Benedict | 30/341 |
| 2,507,535 | 5/1950 | Madsen | 285/921 |
| 2,518,994 | 8/1950 | Miller . | |
| 3,001,000 | 9/1961 | Wantz | 403/284 |
| 3,217,400 | 2/1960 | Illesy | 285/921 |
| 3,681,844 | 8/1972 | Priest | 30/266 |
| 3,718,350 | 2/1973 | Klein | 285/921 |
| 3,731,684 | 5/1973 | Spiegel | 285/921 |
| 3,784,235 | 2/1974 | Kessler et al. | 285/921 |
| 3,895,636 | 7/1975 | Schmidt | 606/205 |
| 3,920,338 | 11/1975 | Dahl | 400/284 |
| 4,299,030 | 11/1981 | Vickers | 30/266 |
| 4,703,560 | 11/1987 | Brooker | 30/155 |
| 4,760,848 | 8/1988 | Hasson | 606/174 |
| 4,823,463 | 4/1989 | Lemaire | 30/335 |
| 4,881,776 | 11/1989 | Wong | 403/96 |
| 4,896,678 | 1/1990 | Ogawa | 178/751 |
| 4,950,273 | 8/1990 | Brigs | 606/174 |
| 5,026,371 | 6/1991 | Rydell et al. | 606/47 |

OTHER PUBLICATIONS

Websters Dictionary, "Staple", 1984 (Nineth New Collegiate Dictionary) p. 1150.

Primary Examiner—Kyle L. Howell
Assistant Examiner—Scott R. Akers
Attorney, Agent, or Firm—David P. Gordon

[57] ABSTRACT

A Maryland dissectors for insertion through a 5 mm trocar tube is disclosed and generally includes a hollow extended aluminum tube, a clevis, a pivot pin, a push rod, Maryland dissector end effector blades, and an actuator for causing reciprocal motion of the push rod. The clevis fixedly engages a first end of the aluminum tube, with the clevis having a hollow bore communicating with the aluminum tube and a pair of parallel, spaced apart, opposed arms extending away from the aluminum tube. The pivot pin extends transversely between the arms of the clevis and engages the clevis arms. The Maryland dissector end effector blades extend away from the aluminum tube and curve away from the longitudinal axis of the aluminum tube. The pivot pin extends through through-holes in the blades which are sized to permit pivotal movement of the blades around the pivot pin and to permit limited angular displacement of the blades relative to the pivot pin. When the Maryland dissector instrument is inserted through the 5 mm trocar tube, the blades angle relative to the pivot pin, and the aluminum tube resiliently flexes. When the blades pass out of the trocar tube the aluminum tube reassumes an unstressed position, and the blades can assume a position perpendicular to the pivot pin, with the blades extending past the projected periphery of the trocar tube.

11 Claims, 7 Drawing Sheets

MARYLAND DISSECTOR LAPAROSCOPIC INSTRUMENT

This is a continuation-in-part of U.S. Ser. No. 07/521,766 which is hereby incorporated by reference herein in its entirety.

BACKGROUND OF THE INVENTION

The present invention broadly relates to laparoscopic surgical instruments. More particularly, the invention relates to disposable surgical instruments which include disposable end effectors such as cutters, graspers, and dissectors which are useful in a laparoscopy procedure.

The laparoscopy procedure has recently become a widely practiced surgical procedure. A laparoscopy procedure involves incising through the navel and through the abdominal wall for viewing and/or operating on the ovaries, uterus, gall bladder, bowels, appendix, or general abdominal surgery. Typically, trocars are utilized for creating the incisions. Trocar tubes ar left in place in the abdominal wall so that laparoscopic surgical tools may be inserted through the tube. A camera or magnifying lens is often inserted through the largest diameter trocar tube (e.g. 10 mm diameter) which is generally located at the navel incision, while a cutter, dissector, or other surgical instrument is inserted through a smaller diameter trocar tube (e.g. 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut or stitched with another surgical instrument; all under view of the surgeon via the camera in place in the navel trocar tube.

The laparoscopic tools of the prior art are primarily reusable stainless steel tools. Between each use of a stainless steel tool, the tool must be soaked, scrubbed, and disinfected. The usual procedure is then to dry the tool, wrap it, and put it in a steam autoclave. The tool is kept sterile until just prior to use when it is removed from the autoclave and unwrapped in the locale of the sterile field of use.

While reusable laparoscopic tools have functioned well for their intended purpose, the process of sterilizing the tool is problematic. Small pieces of tissue or organ often become lodged in the end effectors, and much labor is required to ensure that complete sterility is obtained and maintained. In addition, over time, sharp laparoscopic instruments such as a scissors get dull and must be discarded. However, prior to use of a particular instrument, the surgeon is not able to discern the state of the and whether the instrument will satisfy the surgeon's requirements.

SUMMARY OF THE INVENTION

It is therefore an object of the invention to provide disposable laparoscopic surgical instruments.

It is another object of the invention to provide disposable laparoscopic surgical instruments having investment cast end effectors.

IT is a further object of the invention to provide disposable single and double-acting laparoscopic surgical instruments which utilize improved linkage systems.

It is yet another object of the invention to provide disposable laparoscopic surgical instruments which utilize a uniform push rod and handle end, to which any of a plurality of end effectors are attached.

It is even a further object of the invention to provide disposable Maryland dissector suitable for insertion in a 5 mm trocar tube.

Additional objects of the invention include providing disposable laparoscopic surgical instruments of improved design with smooth transitions from an insulating shrink wrap to the end effectors and to the handle.

In accord with the objects of the invention, a disposable laparoscopic surgery instrument generally includes, a tube, a push rod which extends through the tube, an actuating means engaging the tube and the push rod for imparting reciprocal axial motion to the push rod, end effector means coupled to the push rod by linkage means which are also coupled to the push rod, and a clevis coupled to the tube at its proximal end and to the end effector means at its distal end, wherein axial movement of the push rod effects movement of the end effector means in a plane parallel to the longitudinal axis of the push rod. Plastic shrink wrap is preferably utilized to electrically insulate the disposable instrument and extends over the aluminum tube and over at least an adjacent portion of the clevis. The tube and push rod are preferably made of aluminum, the clevis is preferably made of a high-strength aluminum alloy, the actuating means is preferably made of plastic and aluminum, and the end effector means is preferably made of investment cast bronze.

The clevis of the invention is preferably a separately formed clevis having knurled rod-like proximal end for mating with the end of the aluminum tube, and a post-supporting U-shaped distal portion for holding the end effector means. The post in the distal portion is perpendicular to the legs of the U-shaped distal portion and is arranged to extend through hole(s) in the end effector means. In this manner, the blades or prongs of the end effector means are held by, but can rotate around the post. Each leg of the U-shaped distal portion of the clevis also preferably includes a notch which serves as a terminating location for the shrink-wrap. Another aspect of the clevis relates to the forming of the post integral with one of the legs of the distal portion of the clevis.

The end effector means of the invention can take any of many forms, such as, e.g., a scissors, a dissector, or a grasper. Additionally, the end effector means can be double acting or single acting. Regardless of the type of end effector utilized, the end effector is arranged with a hole to accept the post of the clevis so that the end effector can rotate around the post.

According to one aspect of the invention the push rod is flattened on its distal end, and the linkage means which couples the push rod and the end effector is a staple which extends through a hole in the flattened end of the push rod as well as another hole in the proximal end of the end effector. Because the outer tube is positioned at a fixed distance from the rotation hole in the end effector (due to the clevis), when the push rod is moved axially relative to the tube, the end effector cannot move axially. However, because the push rod is also a fixed distance away from another hole in the proximal end of the end effector (due to the staple), movement of the push rod relative to the tube causes rotation of the end effector in a plane. In other words, movement of the push rod relative to the tube causes the hole through the end effector through which the staple extends to rotate along an arc centered at the rotation hole in the end effector through which the post of the clevis extends. Movement in this manner typically effects a cutting, dissecting or grasping action.

Single acting end effectors can include one hole in the flattened end of the push rod and one staple for connecting the moving prong or blade of the end effector to the push rod. A double acting end effector correspondingly includes two holes in the flattened end of the push rod and two staples; one for each prong or blade. If desired, a single acting end effector can eliminate the staple by forming one end of the pull wire into a "dog's leg" and by inserting the dog's leg pull rod end into the hole in the proximal end of the end effector.

According to other aspects of the invention, a 5 mm Maryland Dissector with jaws which are slightly less severely curved than that of the prior art, but with more than a 5 mm tip to top offset is provided. The 5 mm Maryland dissector utilizes an identical push rod, tube, staple connector, and clevis as does the double acting scissors. The through-holes in the jaws through which the post of the clevis extends are slightly larger than the similar through-holes located in the other end effectors of the invention. With the slightly larger holes, when pushing the 5 mm Maryland dissector through a 5 mm trocar tube, the jaws of the Maryland dissector are angularly displaced relative to the clevis. Upon passing through the trocar tube to the surgery situs, the jaws can resume their normal position.

Additional aspects of the invention include: a ferrule which is snapped onto the handle ridge for guaranteeing continuity of insulation from the tube to the handles; a knurled knob handle lever for allowing activation of the lever when the fingers of the surgeon are holding the ferrule area rather than the scissor like gripping handles of the actuator; modifications in shape to the proximal portion of the end effectors for reinforcement purposes; and a single acting scissors which utilizes a zigzag in the push rod instead of a staple connector.

A better understanding of the disposable laparoscopic surgical instruments of the invention, and additional advantages and objects of the invention will become apparent to those skilled in the art upon reference to the detailed description and accompanying drawings.

BRIEF DESCRIPTION OF THE DRAWINGS

FIG. 1 is a side elevation view, partly in section, of a disposable laparoscopic instrument prior to insertion into a trocar tube, and, in partial phantom format, after insertion into a trocar tube;

FIG. 1a-1 is a cross sectional view through the laparoscopic instrument in FIG. 1 at the indicated location;

FIG. 2b is a cross-section view of the device of FIG. 2a;

FIG. 3 is a side elevation view of an alternate clevis embodiment of the invention prior to assembly with end effectors;

FIG. 3a-1 is a side elevation view of the alternate clevis of FIG. 3 in a closed position;

FIG. 4a is a partially broken-away side elevation view of the actuating handle of the disposable laparoscopic instrument of the invention;

FIG. 4a-1 is a partial top view of the actuating handle of FIG. 4a at the indicated location;

FIG. 4b is a rear elevation view of the device of FIG. 4a;

FIG. 5a is a side elevation view, partly in section, of a double acting dissector in conjunction with the clevis and the distal ends of the rod and tube of the disposable laparoscopic instrument of the invention;

FIGS. 5a-1 and 5a-2 show a perspective view of the staple linkage means of FIG. 5a;

FIG. 5b is a plan view of the device of FIG. 5a;

FIG. 5c is an enlarged side view of the connection of the distal end of the rod and the proximal ends of the staple linkage means of FIG. 5a;

FIG. 6b is a side elevation view of a second embodiment or a single acting scissors:

FIG. 6b-1 shows a perspective view of the push-rod, end effector connection of the single acting scissors of FIG. 6b;

FIGS. 7a-1, 7a-2, and 7a-3 show the relationship between the clevis post and the end effectors of the Maryland dissector of FIG. 7a when the Maryland dissector is being inserted through a trocar tube, and when the push rod of the Maryland dissector is being moved in the direction of the indicated arrows respectively;

FIG. 7b is a plan view of the Maryland dissector of FIG. 7a;

FIG. 8a is a plan view of one element of an investment case end effector in accordance with the present invention:

FIG. 8a-1 is a perspective view of the indicated portion of the investment cast end effector of FIG. 8a;

FIG. 8b is a side elevation view of the device of FIG. 8a;

FIG. 9a is a side elevation view in section of a ferrule shielding device of the present invention engaged with the shrink wrapped aluminum tube and handle of the invention; and FIG. 9b is a cross-section view of the device of FIG. 9a.

DETAILED DESCRIPTION OF THE PREFERRED EMBODIMENT

Figures 1, 1A:
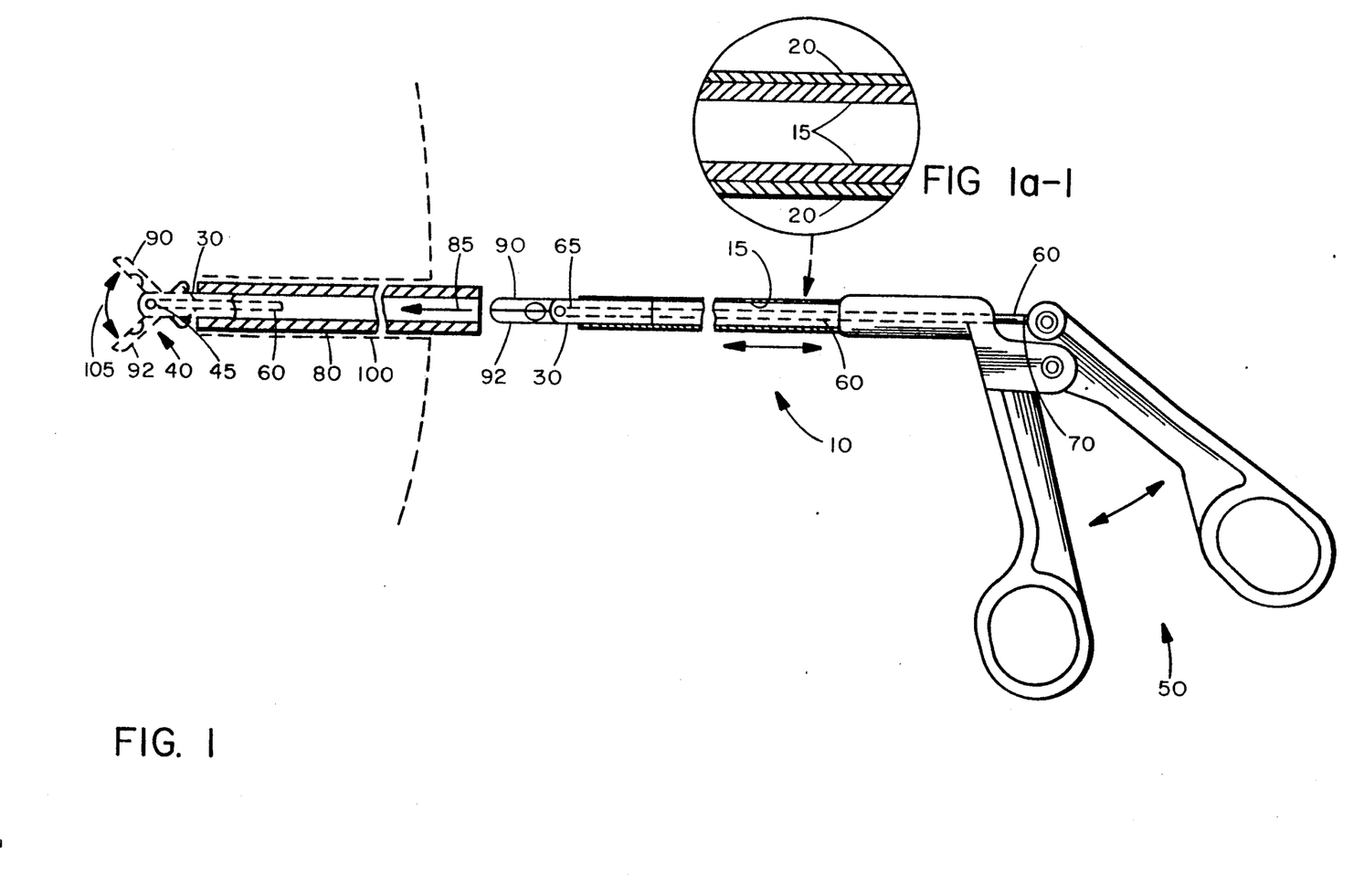

With reference to FIG. 1 (and FIG. 1A-1), a disposable laparoscopic surgical instrument is indicated at 10. The disposable laparoscopic surgical instrument 10 broadly comprises an aluminum tube 15 surrounded by a peripheral insulating shrink wrap layer of plastic 20, a clevis means 30, end effectors 40, actuating means 50, and a push rod 60. The clevis means 30 is advantageously a separately formed aluminum piece which fixedly engages aluminum tube 15 as described in more detail hereinafter. The clevis 30 also engages the end effectors 40 which are pivotally engaged to clevis 30 at pivot pin 45. The end effectors 40 are preferably formed of investment cast bronze as disclosed in copending U.S. Ser. No. 07/521,766 which was previously incorporated by reference herein. The push rod 60, which is also formed of aluminum, is engaged at its distal end 65 to the end effective 40, as hereinafter more fully described, and is connected at 70, at its proximal end to a manually operable actuating means 50. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site.

In use, the laparoscopy instrument 10 is inserted with the blades or graspers 90, 92 of the end effector 40 in the closed position, into trocar tube 80, as indicated at the arrow 85 of FIG. 1. The distal portion of the instrument 10 passes through the trocar tube 80 into body incision 100. Upon the distal portion of the laparoscopy instrument 10 exiting the trocar tube 80, the blades 90, 92 can be opened and closed as indicated at 105 by reciprocal motion of push rod 60 which results from operation of the manual actuating means 50. As is discussed more fully hereinafter, the clevis effectively translates the reciprocal motion of the push rod 60 into the end effector means action indicated at 105.

Figure 2A:
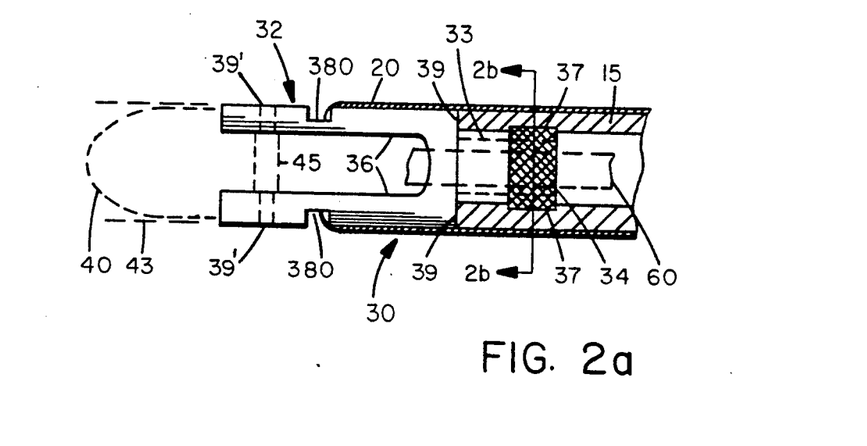
FIG. 2a is a side elevation view, partly in section, of the clevis of the invention in conjunction with the distal end of the tube and shrink wrap of the invention.
Figure 2B:
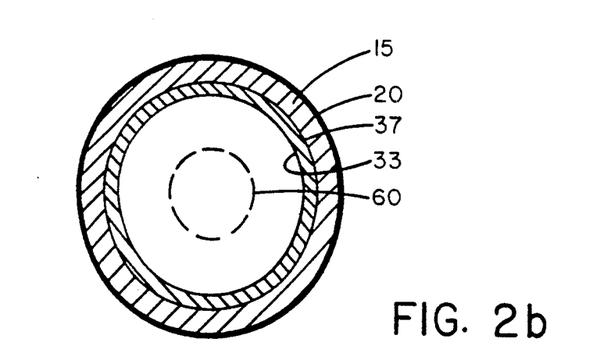

Turning to FIGS. 2a and 2b, a preferred configuration of the clevis 30 of the present invention is seen. The clevis has a knurled rod-like proximal portion 34 for mating with the end of the aluminum tube 15, and a post-supporting U-shaped distal portion 32 for holding the end effector means. The outer diameter of the distal portion 32 of the clevis is larger than the outer diameter of the proximal portion 34; shoulder 39 being formed therebetween. The proximal portion 34 of the clevis is preferably hollow, as indicated at 33, to permit the push rod 60 to extend therethrough. The distal portion 32 of the clevis 30 is provided with legs 36 and a post or pivot pin 45. The post 45 is generally perpendicular, i.e. transverse, to the legs 36 of the clevis and is arranged to extend through hole(s) 39 in the end effector mean 40. In this manner, the blades or prongs of the end effector means 40 are held by, but can rotate around, i.e. are rotatably engaged with the post 45.

As seen in FIG. 2a, a recess or notch 380 is provided which extends across each leg 36 of the clevis 30. Consequently, a peripherally applied electrically insulating plastic wrap 20 can be end-cut at recess 380 and a smooth transition from the end effector means 40 via the clevis 30 to tube 15 can be achieved. Even if slight outward flaring of wrap 20 occurs at the end-cut, as is common, this flaring can be tolerated as it will be within the envelope of the normal outer surface indicated at 43.

Clevis 30 is preferably made from a high strength aluminum base alloy (e.g. 2024 alloy of Alcoa) which is preferably harder than the aluminum base alloy (e.,g. 6061 or 6063 alloys of Alcoa) from which tube 15 is fabricated. The post portion of the clevis may be made out of the identical alloy or, for added strength, out of a stainless steel nail. In assembly of the laparoscopy surgical instrument 10, serrated or knurled portion 34 of clevis 10 is fit snugly into tube 15 such that the walls of tube 15 abut the peripheral shoulder 39 of clevis 30, with the outer surface of tube 15 and the adjacent outer surface of clevis 30 having essentially the same diameter. Mechanical pressure is then applied to tube 15 peripherally at the location of knurled portion 34, thereby crimping the end portion of tube 15 onto the knurled portion 34. Mechanical pressure causes the projections of the knurls to bite into and firmly engage tube 15 as indicated at 37 due to the higher hardness of the clevis material once the clevis 30 and tube 15 have been properly joined, the plastic shrink wrap 20 can be applied over the tube 15 and an adjacent portion of the clevis 30 and end-cut at recess 380.

Figures 3, 3A:
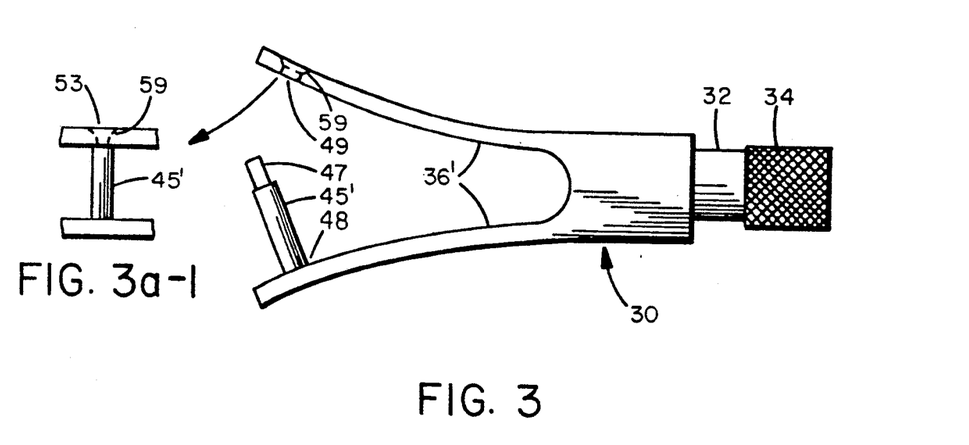

FIG. 3 shows an alternate embodiment for the clevis means of the present invention wherein the clevis 30 is formed and machined from aluminum base alloy as one integral element. As seen in FIG. 2b, the arms 36' of clevis 30 are bent outwardly away from each other. Pivot pin 45' is integral with one arm 36' as indicated at 48 and has a terminal portion 47 of reduced diameter which will engage slightly larger hole 49 when the arms 36 are bent inwardly and parallel with each other (i.e. after end effectors 40 of FIG. 2a are attached). Upon bending of the arms 36', the tip of terminal portion 47 engages and is suitably flattened in recess 59 as indicated at 53 of FIG. 3a-1.

Figures 4A, 4A, 4B:
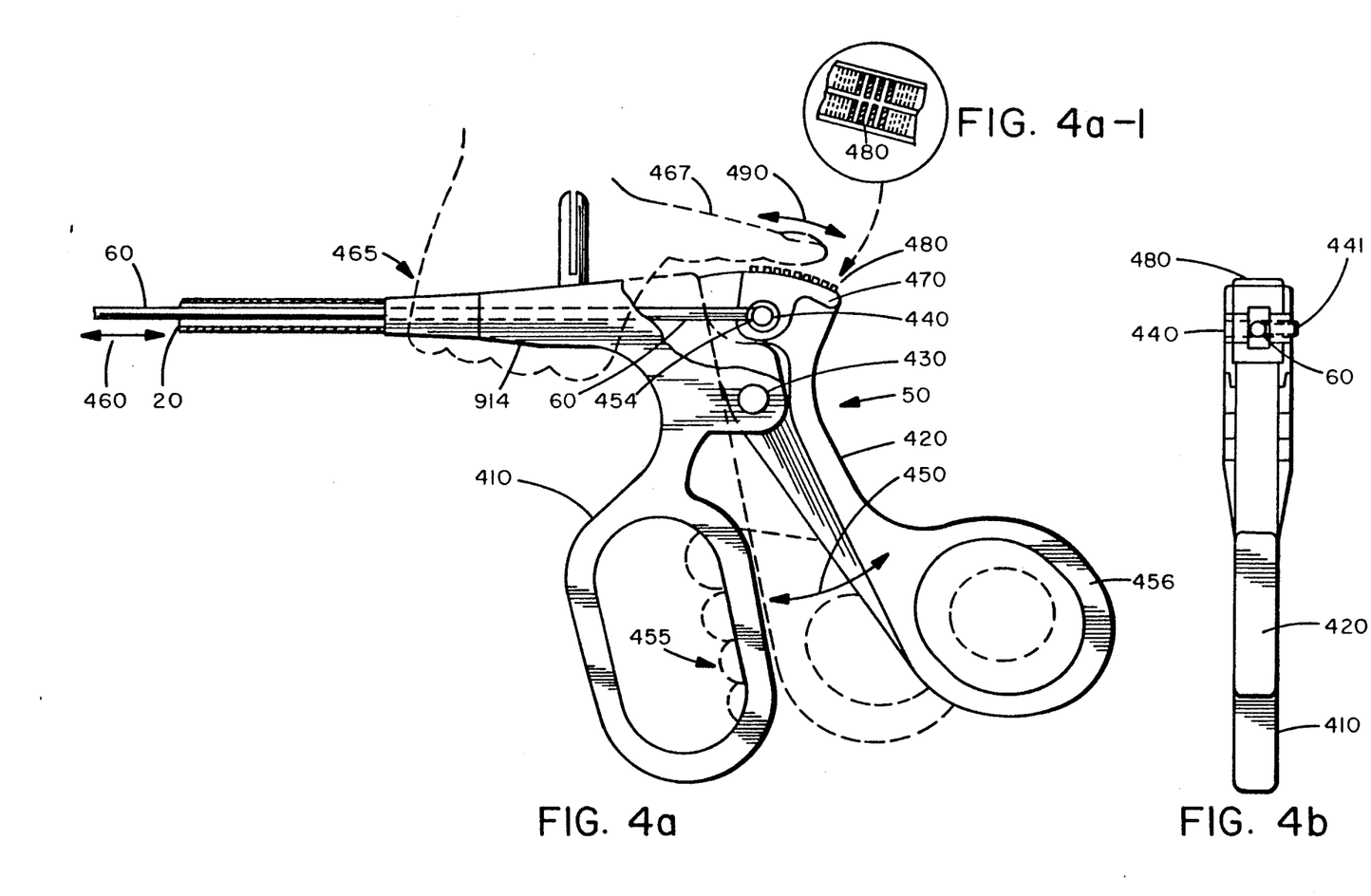

With reference to FIGS. 4a, 4a-1, and 4b, manually operable actuating means are indicated at 50 which includes an electrically insulating housing 914 having a fixed handle portion 410 integral therewith and a lever portion 420 pivotally engaged to housing 914 at pivot pin 430. Push rod 60 passes through aluminum tube 15 (covered by shrink wrap 20) and engages cross pin 440 at 454; set screw 441 being used to extend into cross pin 440 and set push rod 60 in the cross pin 440. The cross pin 440 is fixedly positioned in lever member 420. Upon pivotal motion of lever arm 420, as indicated at 450, using a conventional hand grip as indicated at 455 to apply pressure to extended handle element 456 of lever member 420, push rod 60 will move linearly as indicated at 460 to actuate an end-effector (not shown in FIG. 4a) coupled thereto as hereinabove described. There may be occasions, in the course of certain laparoscopic procedures, that certain surgeons will prefer to hold the actuating means 50 in the manner indicated at 465 with fingers grasping housing 914 and the thumb 467 adjacent portion 470 of lever member 420 which is positioned on the opposite side of cross-pin 440 from extended handle element 456. Thus, in accord with one aspect of the invention, a roughened knurled or serrated surface 480 is provided integral with portion 470 of lever member 420 to enable a frictional engagement with thumb 467. Utilizing serrated surface 480, when thumb motion as indicated at 490 is initiated, pivotal motion of lever arm 420 is accomplished, as indicated at 450, as is the linear motioon of push rod 60 as indicated at 460.

With reference to FIGS. 5a-5g, details are seen of an end effector 40 and the linkage means for linking the end effector 40 to the push rod 60. In particular, in FIGS. 5a-5g, a double acting dissector is shown with blades 90', 92' which are respectively rotatably mounted on pivot pin 45 of clevis 30'. Each blade 90', 92' of the dissector has a forwardly extending manipulating portion 94, and a rearwardly extending planar base portion 96 with a through-hole 98. Each of the through-holes 98 of planar base portions 96 is separately engaged by a separate connecting or linkage means 110, 112.

Figures 5A, 5A, 5A:
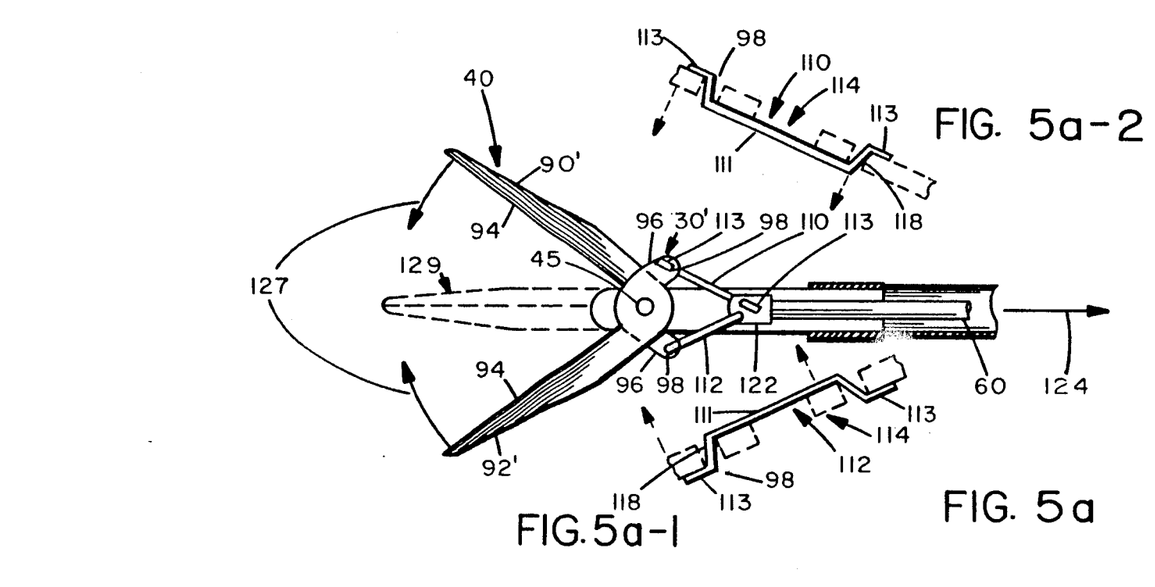
Figure 5B:
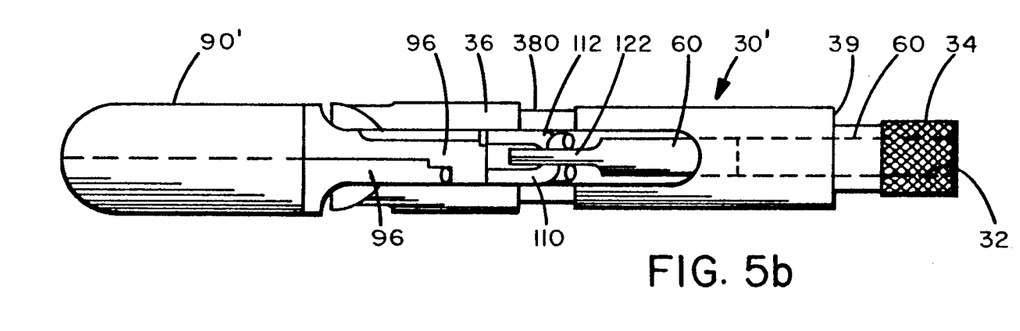
Figure 5C:
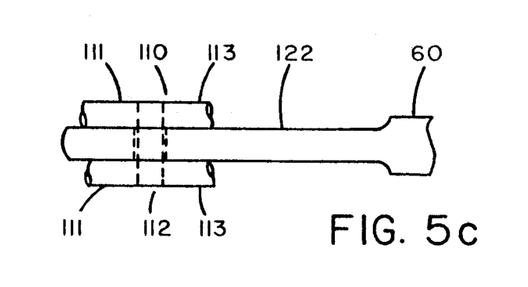
Figure 5D:
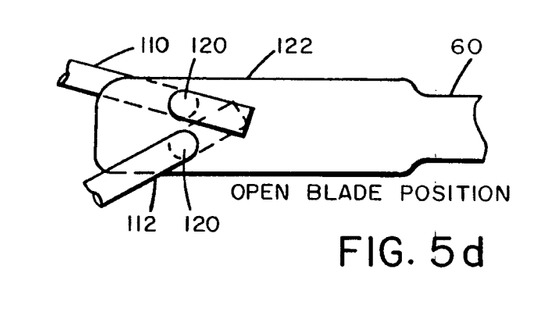
FIGS. 5d and 5e are enlarged top views of the distal end of the rod and the proximal ends of the staple linkage means when the blades of the the double acting dissector are in open and closed positions respectively.
Figure 5E:
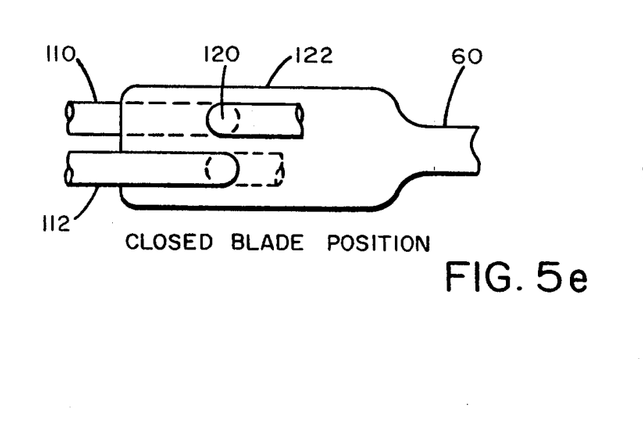

As shown in FIG. 5a, FIG. 5a-1, and FIG. 5a-2, according to one preferred embodiment, each linkage means 110, 112 is in the form of a thin metal member generally in the shape of an outwardly flared staple. Each linkage means may be generally described as having a U-shaped section 114 with a base 111 perpendicular to and bridging the arms 118 of the U, and two generally parallel spaced apart outwardly extending side or tab elements 113 which are generally parallel to base 111. Each of the linkage means 110, 112 has one of its tab elements 113 engaged in a through-hole 98 of a planar base 96, with the U-shaped section of the linkage means extending respectively in opposite directions as illustrated. The other tab element 113 of the linkage means 110, 112 engage through-holes 120 formed in a flattened plate-like terminal portion 122 of push rod 60 (as seen more clearly in FIGS. 5d-5f). As can be seen from FIG. 5a, movement of push rod 60 in the direction indicated at 124 will cause blades 90', 92' to move in the direction indicated at 127 to the position 129 without interference between the oppositely positioned staple-like linkage means 110, 112. Correspondingly, the tab elements 113 of the linkage means 110, 112 which extend through the flattened terminal portion 122 of push rod 60 will move from their position shown in FIG. 5d, to the position shown in FIG. 5e.

That manipulators (blades) 90' and 92' open and close in response to the axial movement of push rod 60 may be understood by understanding the relationship of the clevis 30' and linkage means 110, 112 to the blades 90', 92', the push rod 60, and the tube 15. In particular, due to the fact that the clevis 30' is rigidly attached to the tube 15 (as described above with reference to FIG. 2a), the tube 15 is a fixed distance from the rotation pin 45 of the clevis, and hence to the holes in the blades 90' and 92' through which rotation pin 45 extends. Thus, when the push rod 60 is moved axially relative to the tube 15 (the tube being fixed in place), the blades of the end effector cannot move axially with the push rod. However, because the push rod 60 is also a fixed distance away from holes 98 in the base portion of the end effector blades (due to staple linkage means 110, 112), movement of the push rod relative to the tube must cause movement of the holes 98 in the end effector blades. Because one part each blade is fixed, but another part must move when the push rod 60 is moved relative to the tube 15, end effector blades 110 and 112 rotate along an arc centered at the fixed rotation hole in the end effector through which the post 45 of the clevis 30' extends. Movement in this manner typically effects a cutting or grasping action.

Figure 5F:
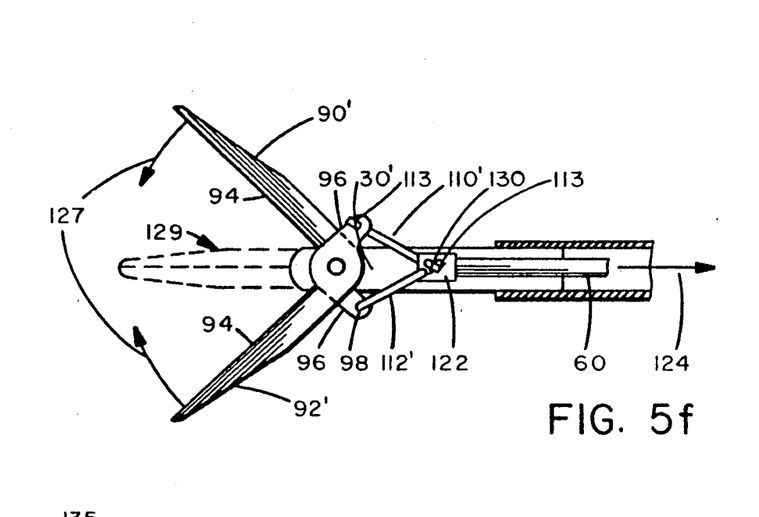
FIG. 5f is a side elevation view of a double acting dissector utilizing a crossed staple linkage means.
Figure 5G:
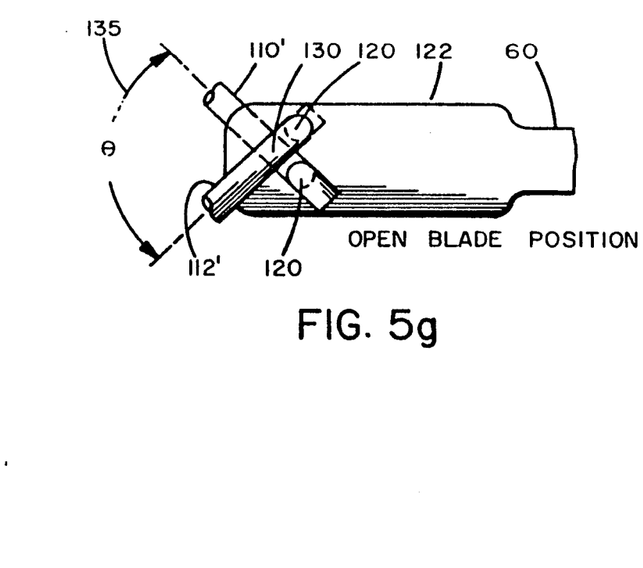
FIG. 5g is an enlarged top view of the distal end of the rod and the proximal end of the crossed staple linkage means

FIGS. 5f and 5g show another embodiment of the linkage means which increases the stability of the end effector means 40. In FIGS. 5g and 5h it is seen that the linkage means 110', 112' do not respectively engage the nearest of the through-holes 120 transversely aligned in the plate-like terminal portion 122 of push rod 60, but instead cross-over as indicated at 130. With this arrangement the angle θ, indicated at 135, is increased. The increase in this angle affords a more stable instrument, because the amount of "shake" which results from the unavoidable clearances at the pivot 45 is reduced; i.e., as θ approaches 90°, the amount of free movement at the end of an end-effector bade 90', 92' is minimized.

Figure 6A:
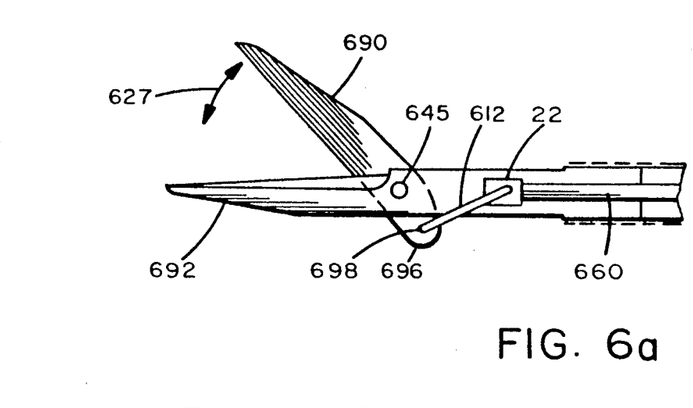
FIG. 6a is a side elevation view of a first embodiment of a single acting scissors of the invention in conjunction with the clevis, and the distal ends of the rod and tube of the disposable laparoscopic instrument of the invention.

FIGS. 6a shows a single acting scissors. Essentially, the single acting scissors is identical to the double acting scissors of FIGS. 2a-2g except that blade 692 is stationary; hence no staple is used to connect blade 692 to rod 660. While blade 692 is stationary, blade 690 pivots as indicated at 627 around pin 645. To ensure rotational movement of blade 690 upon axial movement of rod 660, the end 22 of rod 660 should be supported.

Figures 6B, 6B:
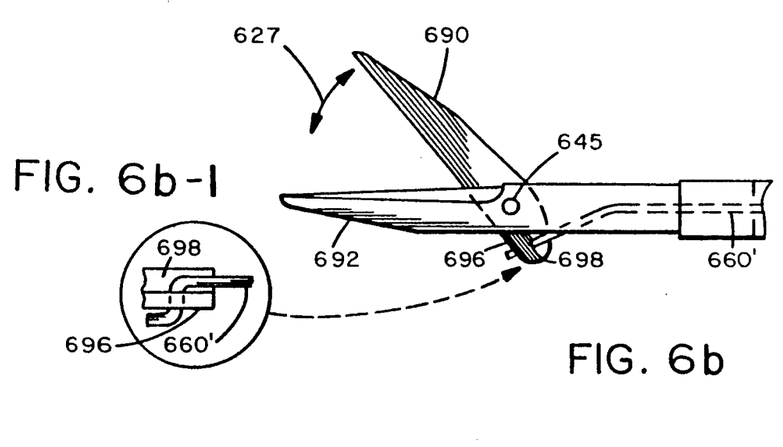
Figure 7A:
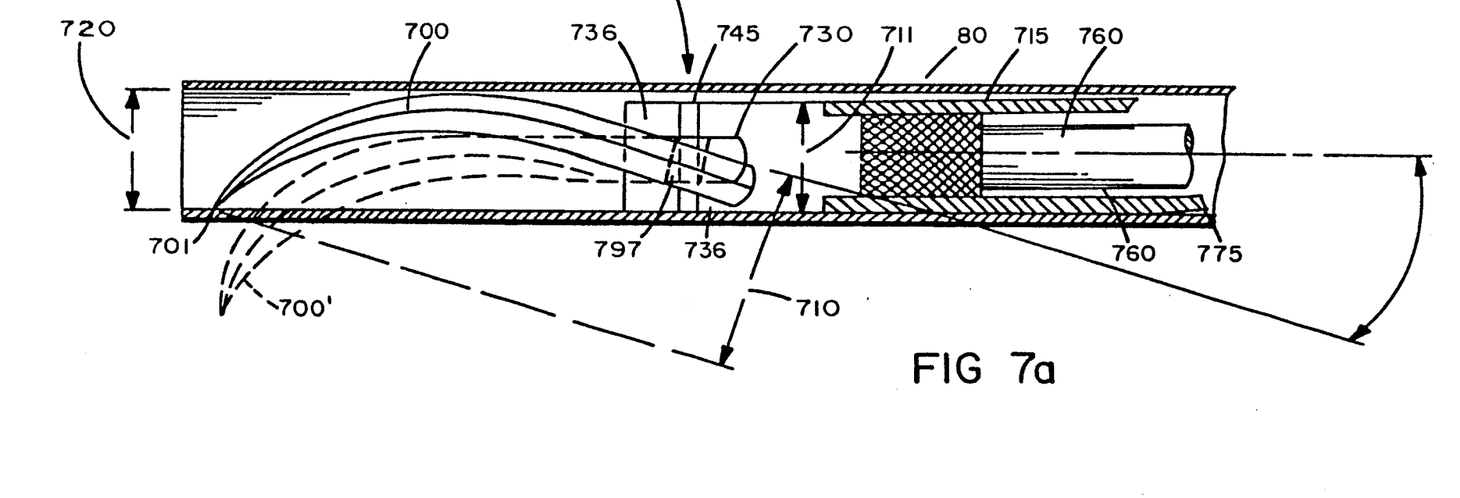
FIG. 7a is an elevation view in cross-section of a Maryland dissectors according to the invention.
Figure 7A:
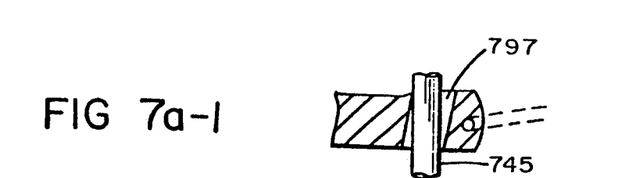
Figure 7A:
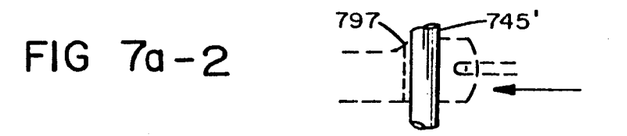
Figure 7A:
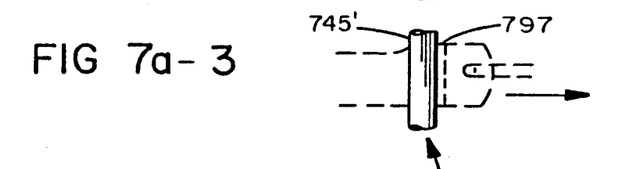
Figure 7B:
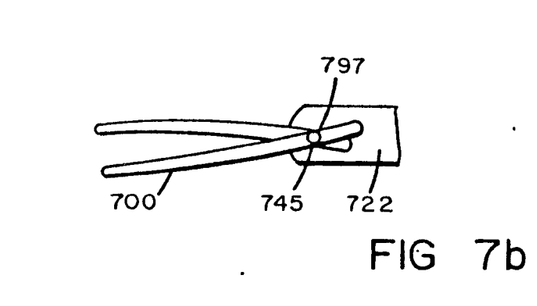

FIGS. 6b and 6b-1 shows a preferred embodiment of a single acting scissors where instead of utilizing a pull rod with a flattened end, pull rod 660' is a very thin wire of staple thickness (e.g. 25 mils) which has a rigid dog's-leg or zigzagged end which extends through hole 698 of the proximal end of scissor blade 690. A similar pull rod is shown in previously incorporated U.S. Ser. No. 07/521,766, where instead of a single acting scissors, a radial jaw biopsy forceps is shown.

With reference to FIGS. 7a, 7a-1, 7a-2, 7a-3, and 7b a disposable laparoscopic Maryland dissector for use in a 5 mm diameter trocar tube 80 is shown; the actual inner diameter 720 of a "5 mm" trocar tube typically being about 6 mm). Traditionally, relatively large trocar tubes (e.g. 10 mm) are required when using Maryland dissectors, as the distance from the blade tips 701 to the top of rod (i.e., the width of the curved jaws as indicated at 710) is relatively large. Of course, larger trocar tubes inflict more trauma on the patient. Thus, it is desirable to be able to place a Maryland dissector in a smaller diameter trocar tube, e.g. a 5 mm trocar, such as indicated at 720.

In conjunction with curved jaws or blades 700, the 5 mm Maryland dissector of the invention preferably utilizes an actuator mechanism such as shown in FIGS. 4a and 4b, tube 715, push rod 760, linkage means such as shown in FIG. 5a, and clevis 730 which are substantially identical to the double acting equivalent devices seen in the double acting dissector embodiments of FIG. 1 and FIGS. 5a-5g. In the Maryland dissector of the present invention, the curve of jaws 700 is slightly less severe than a standard Maryland Dissector. However, the less severe curve does not by itself permit accommodation in a 5 mm trocar tube. Rather, the pivot holes 797 in the end effector blades of the Maryland dissector are arranged to be large enough to accommodate the required angular displacement (as indicated by angle B in an exaggerated manner) of the blades relative to the clevis and pivot axle 745. In other words, extra clearance is provided where pivot axle 745 of the clevis 730 fits into the rear portion of the end effector such that the end effectors can assume an angled position of preferably up to eight degrees (745) when the Maryland dissector is being pushed through trocar tube 80, and can assume their normal position (745') which is substantially parallel to the arms 736 of the clevis 730 when the jaws 700 have passed through the trocar tube 80 and have assumed their normal position (700'). In addition, the flexibility of the aluminum tube, which is greater than that of a stainless steel tube which is used in traditional instruments, allows freedom for the curved instrument to pass through the trocar tube as indicated at 775.

Figures 8A, 8A:
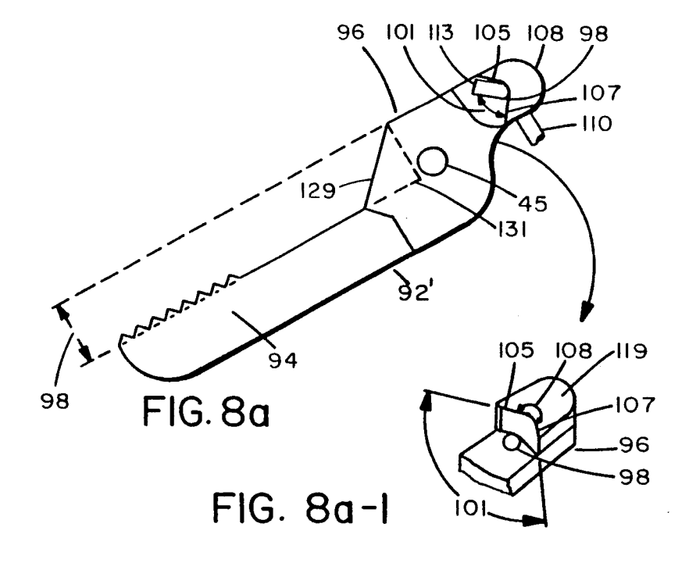
Figure 8B:
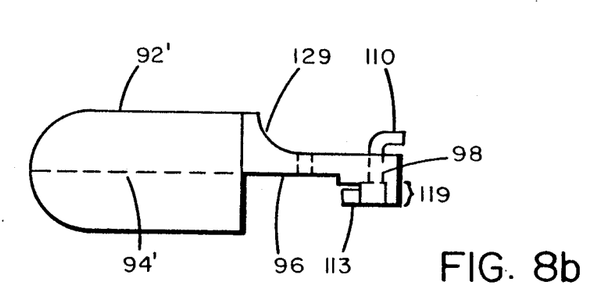

With reference to FIGS. 8a, 8a-1, and 8b, when an investment castable metal, such as bronze, is used in the making of an end effector 92', all features of the end effector are formed during casting to provide an integral end effector element. This is in contrast with the prior art practice of stainless steel end effectors which involved forging and machining to achieve the desired finished forms. While stainless steel is stronger than bronze, the use of investment cast bronze eliminates the need for forging and machining and also abrasive blasting and pickling and other treatments required in stainless steel fabrication which interfered with the achievement of close tolerances. Since investment cast bronze while of considerable strength, is not as strong as stainless steel, it is advantageous to provide a novel configuration for the end effectors, e.g. 92', by including integral reinforcing elements in the investment cast end effector. In FIGS. 8a and 8b the extended cutting portion 94 and the base portion 96 are conventionally laterally offset as indicated at 98. In the prior art, the offset portions 94,96 join at essentially a right angle whereas in the present invention an integral mass of investment cast metal, in the form of a fillet 129, bridges the offset base and cutting portions and significantly strengthens the end effector. As shown in FIG. 8a, the flared staple linkage means 110 pivotally rotates in through-hole 98 in the base end effector portion 96, with its tab element 113 rotating through the angular segment 101 defined by radii 105, 107 extending from through-hole 98. Angular segment 101 is less than 180° of arc, e.g. typically 90°-120°. The supplementary arc segment 108 is more than 180°, typically 240° to 270°, which is the angular difference between segment 101 and 360°. Segment 108 is filled with an integral mass of cast metal 119 adjacent and enveloping through-hole 98 which strengthens base 96 but does not interfere with the rotation of flared element 113. The height of the segmental metal mass 119 is preferably at least equal to the diameter of tab element 113.

With reference to FIGS. 9a and 9b, and in reference to another aspect of the invention, a ferrule type connecting means 910 is shown. Ferrule 910 provides a secure electrically insulating connection which peripherally bridges the exposed peripheral, electrically conductive, lateral portion 912 of aluminum tube 20 located between electrically insulating plastic shrink wrap 20 and the electrically insulating housing 914 of manually operable actuating means 50 which closely surrounds the aluminum tube 15. The portion of electrically insulating housing 914 adjacent the terminal portion 916 of electrically insulating shrink wrap 20 is provided with a flat-surfaced peripheral ridge 920. Ridge 920 has a substantially perpendicular wall 922 in the direction away from the shrink wrap 20. Wall 922 forms one side of a frusto-conical peripheral groove 921 which slopes upwardly away from perpendicular wall 922 until it terminates at wall 923. Ridge 920 further has a substantially frusto-conical surface 924 which slopes toward and is closely adjacent but slightly spaced from the shrink wrap 20 as indicated at 926.

Ferrule means 910 has a generally conical outer surface 929. The inner surface of ferrule means 910 is provided with a cylindrical passage 930 which is adapted to be closely adjacent to and surround a portion of shrink wrap 20, and is slidable with respect thereto. Contiguous to cylindrical passage 930, and coaxial therewith, is an outwardly flaring frusto-conical passage 932 which bridges and is spaced from the peripheral electrically conductive portion 912 of aluminum tube 20. Outwardly flaring frusto-conical passage 932 is bounded at its wider flared end by a flat peripheral rim of extension 934 which is adapted to abut the flat surfaced peripheral ridge 920 of the portion 914 of the electrically insulating housing 50. An axially inwardly depending perpendicular peripheral wall 936 of the outwardly flaring frusto-conical projection 938 abuts the peripheral wall 922 of the electrically insulating housing 914 of actuating means 50. Projection 938 is matingly seated in the extended frusto-conical peripheral groove 940 of the housing 914 and causes the ferrule connecting means 910 to be secured to the housing 914 while shielding the electrically conductive peripheral portion 912 of aluminum tube 20.

Ferrule connecting means 910 is suitably made of a strong, resilient, electrically insulating plastic material such as polypropylene or polycarbonate. In a preferred embodiment, the ferrule is a colored plastic, with the color utilized to identify the type of instrument of which it is a part. For example, a blue ferrule might identify a Maryland dissector, while a red ferrule might identify a single acting scissors. Regardless of color, the ferrule is installed by being moved slidably along shrink wrap 20 in the direction indicated at 945. When the ferrule means 910 is moved in the direction indicated, at some point, the portion of the frusto-conical projection 938 located adjacent wall 936 resiliently deforms outwardly to pass over rim 934 of rigid plastic housing 914. After wall 936 passes wall 922, the frustoconical projection 938 snaps back into a mating engagement with groove 940 of the rigid plastic housing 914. In this mated position, the electrically insulating ferrule connecting means 910 overlaps peripheral electrical conductive portion 912 of aluminum tube 20 as well as substantial portions of the electrically insulating shrink wrap 20 and the electrically insulating housing 914. In this manner, the ferrule connecting means 910 ensures that the possibility of short circuiting and electrical disruption is eliminated.

The preferred laparoscopy instruments of the invention are preferably assembled in the following fashion. The knurled portion 34 of the clevis 30 of the invention is inserted into the aluminum tube 15 which had been previously insert molded in the fixed handle portion 914, 410 of the actuating means 50. The aluminum tube 15 is crimped over the knurls 37 to effect mating. Shrink wrap 20 is then applied over the aluminum tube 15 and endcut at grooves 380 in the arms 36 of the clevis 30. Ferrule 910 is slid over the distal end of the aluminum tube 15, up over the end of the housing 914, and snapped into place, thereby providing complete insulation. The rod 60, staples 110, 112, and end effectors (e.g. 90, 92) are assembled, with the staples coupling the rod to the end effectors. The rod is slid through the clevis and down the aluminum tube, until the end effectors are located between the arms of the clevis. When the holes in the proximal end of the end effectors (e.g. 96, 98) are lined up with the through-holes 39 in the arms of the clevis, the rotation post 45, which may either be integral with the clevis, or a separate post or nail, is inserted through the holes in the end effectors, and secured in the holes of the clevis arms such as by tapping. At this point, all that remains to be assembled is the actuating means 50. To assemble the actuating means, a cross pin 440 is inserted in handle 420. Handle 420 is then arranged such that the push rod 60 which extends out of the fixed handle portion will extend through the cross pin 440. With rod 60 in the cross pin 440, handle 420 is lined up with handle 410 such that the handle rotation pivot pin 430 can be inserted. With pivot pin 430 in place, and with the end effectors in the closed position, set screw 441 is tightened into the cross pin until it bites into rod 60, thereby holding rod 60 in place relative to cross pin 440.

There has been described and illustrated herein a disposable laparoscopic instrument. While particular embodiments of the invention have been described, it is not intended that the invention be limited exactly thereto, as it is intended that the invention be as broad in scope as the art will permit. Thus, while particular end effectors were disclosed, it will be appreciated that other end effectors such as, e.g., duck-bill graspers, duck-bill dissectors, atraumatic graspers, and traumatic (rat-tooth) graspers, could be utilized. Also, while various materials were described as being preferred for various parts, it will be appreciated that other materials could be utilized. By way of example only, and not by way of limitation, while the tube and clevis are preferably made from aluminum alloys, with the clevis being harder than the tube, if desired, the tube could be harder than the clevis. In such a situation, rather than crimping the tube over the clevis, the clevis could be welded or press fit into the tube. Therefore, it will be apparent to those skilled in the art that other changes and modifications may be made to the invention as described in the specification without departing from the spirit and scope of the invention as so claimed.

What is claimed is:

1. A surgical instrument for insertion through a trocar tube comprising:
   a) a hollow extended tube having first and second ends and a longitudinal axis;
   b) a clevis means fixedly engaged to said first end of said hollow extended tube, said clevis means having a hollow bore opening to said hollow extended tube and a pair of parallel, spaced apart, opposed arms extending away from said hollow extended tube and being substantially within the projected periphery of the hollow extended tube;
   c) a pivot means extending substantially, transversely between said arms and engaging said arms, said pivot means having a first diameter; p1 d) an end effector means having a through-hole means through which said pivot means extends, said through-hole means having a second diameter larger than said first diameter for permitting pivotal movement of said end effector means around said pivot means and for permitting limited angular displacement of said end effector means relative to said pivot means, said end effector means having two blade elements which extend away from said hollow extended tube and which curve away from the longitudinal axis of said hollow extended tube thereby extending outside of a projected periphery of the trocar tube when said blade elements extend past the trocar tube, but which are within the periphery of the trocar tube upon an angular displacement of said blade elements relative to said pivot means when said blade elements are inside the periphery of the trocar tube; and
   e) actuator means coupled to said end effector means and to said hollow extended tube for imparting motion along said longitudinal axis to said end effector means relative to said clevis means which motion is translated at said clevis means to pivotal motion of said blade elements.

2. A surgical instrument according to claim 1, wherein:
said hollow extended tube is a resilient tube comprised of aluminum which resiliently bends when said end effector means are angularly displaced relative to said pivot means.

3. A surgical instrument according to claim 1, wherein:
said end effector means are Maryland dissector means.

4. A surgical instrument according to claim 3, wherein said trocar tube is a five millimeter trocar tube, and wherein:
said resilient aluminum tube has a diameter of at most approximately five millimeters.

5. A surgical instrument according to claim 4, wherein:
said second diameter of said through-hole permits angular displacement of said end effector means relative to said pivot means of at most approximately eight degrees.

6. A surgical instrument according to claim 2, wherein said trocar tube is a five millimeter trocar tube, and wherein:
said resilient aluminum tube has a diameter of at most approximately five millimeters, and
said second diameter of said through-hole permits angular displacement of said end effector means relative to said pivot means of at most approximately eight degrees.

7. A surgical instrument according to claim 1, wherein:
said actuator means comprises,
a rod extending at least partially through said extended hollow tube and said hollow bore of said clevis and having a first end and a second end;
connecting means linking said first end of said rod with said end effector means; and
hand-held actuating means engaged to said second end of said rod for imparting reciprocal motion to said rod relative to said tube along said longitudinal axis.

8. A surgical instrument according to claim 7, wherein:
said hollow extended tube, said rod, and said clevis are comprised of aluminum, said actuating means is comprised of plastic, and said end effector means is comprised of investment cast bronze, and said instrument is disposed of after a single use.

9. A surgical instrument according to claim 7, wherein:
said hollow extended tube is a resilient tube comprised of aluminum which resiliently bends when said end effector means are angular displaced relative to said pivot means.

10. A surgical instrument according to claim 9, wherein said trocar tube is a five millimeter trocar tube, and wherein:
said resilient aluminum tube has a diameter of at most approximately five millimeters.

11. A surgical instrument according to claim 10, wherein:
said second diameter of said through-hole permits angular displacement of said end effector means relative to said first means of at most approximately eight degrees.

* * * * *